US00PP32389P2

(12) United States Plant Patent
Olesen

(10) Patent No.: US PP32,389 P2
(45) Date of Patent: Oct. 27, 2020

(54) MINIATURE ROSE PLANT NAMED 'POULPAR122'

(50) Latin Name: ***Rosa* hybrid**
Varietal Denomination: Poulpar122

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,240

(22) Filed: Sep. 4, 2019

(51) Int. Cl.
*A01H 5/02* (2018.01)
*A01H 6/74* (2018.01)

(52) U.S. Cl.
USPC ..... Plt./126

(58) Field of Classification Search
USPC ..... Plt./101, 116, 119, 123, 126
See application file for complete search history.

*Primary Examiner* — Susan McCormick Ewoldt

(57) ABSTRACT

A new garden rose plant of the Miniature class which has abundant, orange flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar122'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpar122', originated as a single seedling from the stated cross.

The new variety may be distinguished from its male pollen parent and female seed parent primarily by the following characteristics. The male pollen parent plant has near white flowers while the new variety has orange blend flowers. The female seed parent plant has yellow flowers while the new variety has orange flowers. The objective of the hybridization of this rose variety was to create a new and distinct variety with unique qualities, such as:

1. Uniform and abundant orange flowers;
2. Vigorous, but compact growth when propagated on its own roots;
3. Exceptional disease resistance.

This combination of qualities is not present in previously available commercial cultivars of this type, known to the inventor, and distinguish 'Poulpar122' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpar122' was selected in the spring of 2013 by the inventor as a single plant from the progeny of the aforementioned hybridization.

Asexual reproduction of 'Poulpar122' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpar122' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar122'.

Specifically illustrated in FIG. 1 of the drawings are open flowers, petals detached, flower buds, and sepals detached revealing reproductive flower parts.

Figure 1:
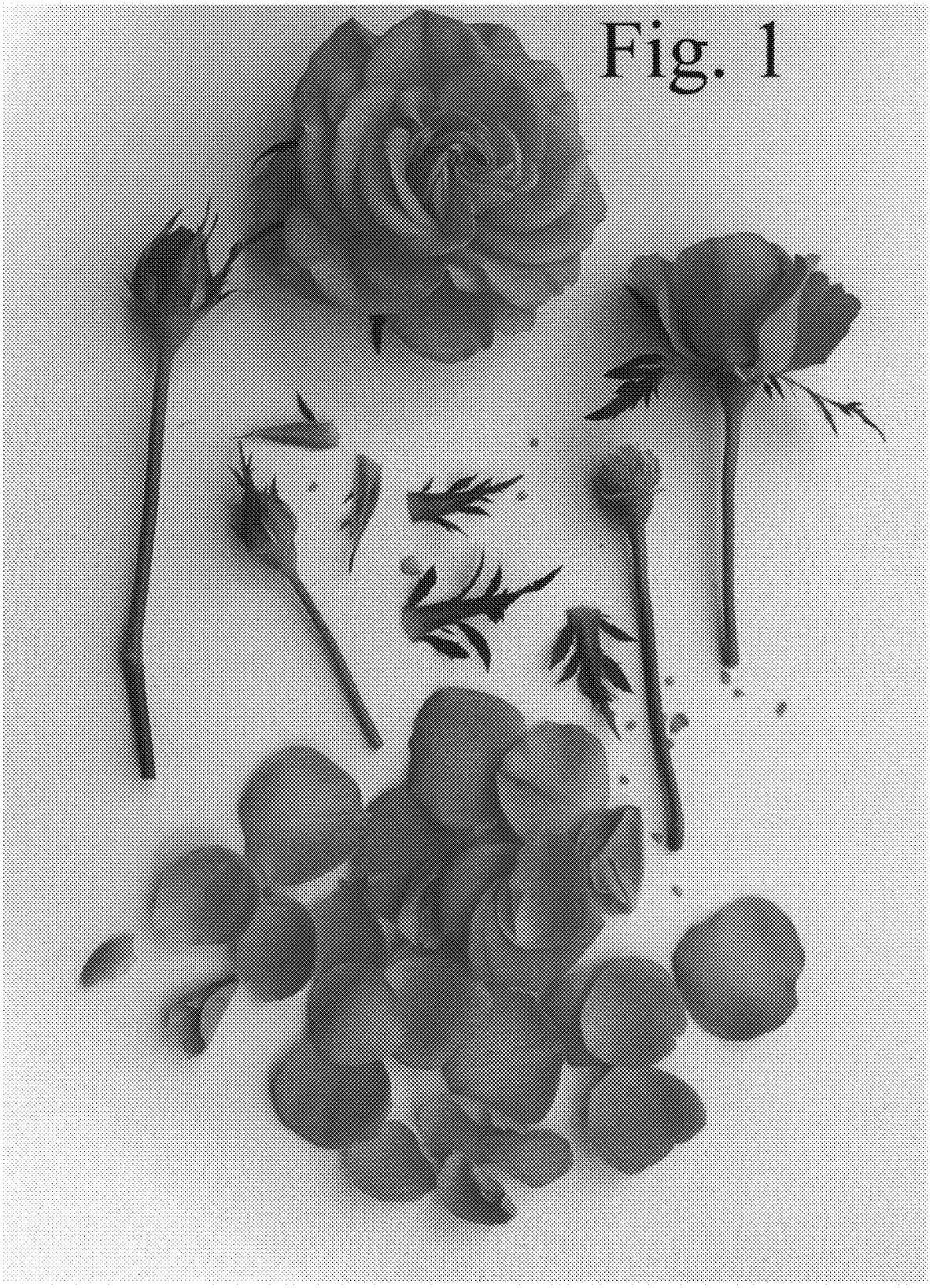
Figure 2:
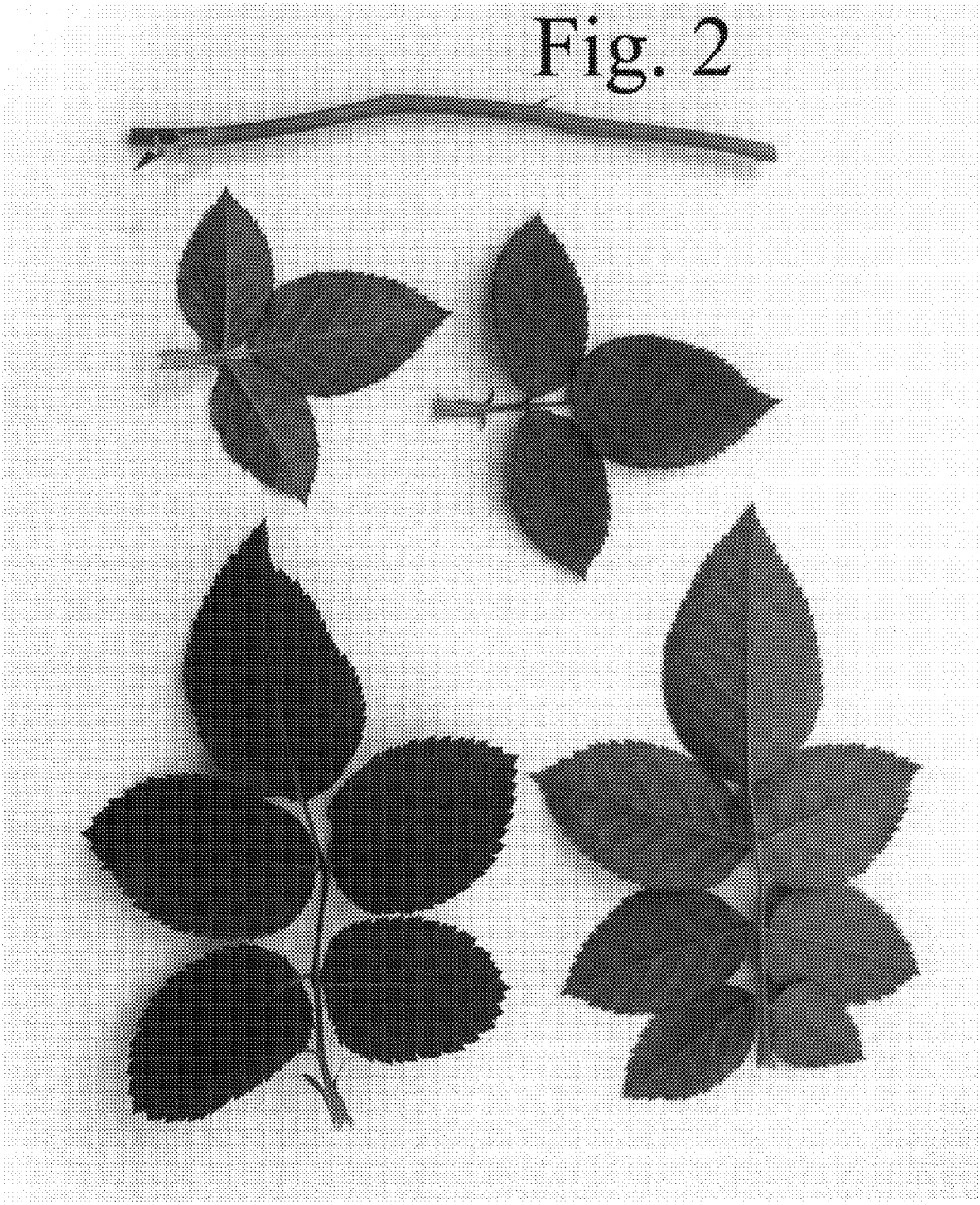

Specifically illustrated in FIG. 2 of the drawings are juvenile and mature leaves and bare stem. Plants shown are 2 years of age.

DETAILED DESCRIPTION OF THE VARIETY

The following is a description of 'Poulpar122', as observed in its growth in a greenhouse in Odense Denmark. Observed plants are 2 years of age, and were grown on their own roots in 24 cm pots. Color references are made using The Royal Horticultural Society (London, England) Colour Chart, 2001, except where common terms of color are used.

For a comparison, several physical characteristics of the rose variety 'Poulpar090', U.S. Plant Pat. No. 28,044 are compared to 'Poulpar122' in Chart 1.

CHART 1

| | 'Poulpar122' | 'Poulpar090' |
|---|---|---|
| Petal Count | 65 petals | 80 petals |
| Flower Diameter | 65 mm | 70 mm |
| General Tonality of Flower Color | Orange-Red Group 30D | Yellow-Orange Group 20D |

FLOWER AND FLOWER BUD

Blooming habit: Continuous.

Flower bud:

*Size.*—Upon opening, 25 mm in length from base of receptacle to end of bud. Bud diameter is 12 mm.

*Bud form.*—Ovoid.

*Bud color.*—As sepals divide petals are Greyed-Yellow Group 162B, and Greyed-Red Group 178D.

*Sepal inner surface.*—Color: Yellow-Green Group 147A. Surface: Lightly pubescent.

*Sepal outer surface.*—Color: Yellow-Green Group 146A. Texture: Smooth.

*Sepal shape.*—Apex: Cirrhose. Base: Flat at union with receptacle.

*Sepal margin.*—Margins have strong foliaceous appendages on three of the five sepals.

*Sepal size.*—30 mm long, 10 mm wide.

*Receptacle.*—Texture: Smooth. Size: 8 mm in height, 10 mm wide. Color: Yellow-Green Group 144B. Shape: Funnel.

*Pedicel.*—Surface: Smooth. Length: 60 mm. Diameter: 3 mm on average. Color: Yellow-Green Group 144B. Strength: Strong.

Flower bud development: Flower buds are borne singly.

Flower bloom:

*Fragrance.*—Moderate to strong perfume.

*Duration.*—The blooms have a duration on the plant of approximately 14 days. Petals fall cleanly away from plant after flowers have fully matured.

*Size.*—Flower diameter is 65 mm when open. Flower depth is 30 mm.

*Flower shape.*—High centered, semi-double, with a high pointed center which is tightly closed.

*Shape of flower, side view.*—The upper portion is flattened convex. The lower portion is flat.

Petalage: Under normal conditions, flowers have about 35 petals.

General tonality of flower: Open flowers are Orange-Red Group 30D.

Petal color:

*Upon opening, outer petals.*—Upper surface: Yellow Group 12A at the basal zone. Orange Group 25B splashed with Orange-Red Group 34C. Lower surface: Yellow Orange 16A, splashed with Orange-Red Group 33C.

*Upon opening, inner petals.*—Upper surface: Yellow Group 12A at the basal zone. Orange Group 25B splashed with Orange-Red Group 34C. Lower surface: Yellow Orange 16A, splashed with Orange-Red Group 33C.

*Basal petal spots, upon opening.*—Upper surface: Yellow Group 12A. Lower surface: Yellow Orange 16A.

*After opening, outer petals.*—Upper surface: Basal and middle zone are Orange-Red Group 31B. Red Group 38A at the petal apex. Yellow Group 12A at basal zone. Lower surface: Yellow Group 13D at the basal zone with other intonations of Orange-Red Group N34D.

*After opening, inner petals.*—Upper surface: Basal and middle zone are Orange-Red Group 31B. Red Group 38A at the petal apex. Yellow Group 12A at basal zone. Lower surface: Yellow-Orange Group 16B lightly splashed with Orange Group 26B. At the basal zone Yellow Group 12A.

*Basal petal spots, after opening.*—Upper surface: Yellow Group 12A. Lower surface: Yellow Group 12A.

Petals:

*Petal reflex.*—None.

*Margin.*—Entire and uniform. Moderate undulations.

*Shape.*—Broad and elliptic. Apex shape: Rounded. Base shape: Rounded.

*Size.*—30 mm (l)×33 mm (w).

*Texture.*—Smooth.

*Thickness.*—Average.

Petaloids:

*Size.*—8 mm (l) by 5 mm (w).

*Quantity.*—About 4.

*Shape.*—Elliptical with an acute base and rounded apices.

*Color.*—The upper surface is Orange Group 25B splashed with Orange-Red Group 35C and Yellow Group 12A at the base of the petaloid. The lower surface is Yellow Orange 16A at the base, splashed with Orange-Red Group 33C.

Reproductive flower parts:

*Pollen.*—None observed.

*Anthers.*—Size: 2 mm in length. Color: Yellow-Orange Group 21A. Quantity: 38 on average.

*Filaments.*—Color: Yellow Group 13A. Length: 4 mm.

*Pistils.*—Length: 8 mm. Quantity: 15 on average.

*Stigmas.*—Color: Yellow Green Group 1C.

*Styles.*—Color: Yellow Green Group 1C.

*Location of stigmas.*—Superior in location relative to the length of the filaments and the height of the anthers.

*Hips.*—None Observed.

PLANT

Plant growth: Upright, bushy. Plants are 30 cm in height, and 25 cm wide.

Stems:

*Color of juvenile growth.*—Yellow-Green Group 144B.

*Color of mature growth.*—Yellow-Green Group 144B.

*Length.*—Canes are about 10 cm from the base of the plant to the flowering portion.

*Diameter.*—About 5 mm.

*Internodes.*—On mature canes about 45 mm between nodes.

*Surface texture.*—Young wood: Smooth. Older wood: Smooth.

Long prickles:

*Incidence.*—2 prickles per 10 cm of stem.

*Size.*—Average length of prickles on mature stems is 5 mm.

*Shape.*—Upper portion is linear. Lower portion is concave.

*Color.*—Juvenile prickles: Yellow-Green Group 144B. Mature prickles: Yellow-Green Group 144B.

Plant foliage:

*Compound leaf.*—140 mm (l)×110 mm (w).

*Quantity.*—2 leaves per 10 cm of stem on average.

*Leaf bearing angle to the stem.*—45 degrees.

*Color of juvenile foliage.*—Upper side: Yellow-Green Group 146A with intonations of Greyed-Red Group 178A at margins. Lower side: Yellow-Green Group 146B with shaded intonations of Greyed-Red Group 178A.

*Color of mature foliage*.—Upper side: Yellow-Green Group 147A. Lower side: Yellow-Green Group 147B.

Plant leaves and leaflets:

*Stipules*.—Size: 8 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 13 mm. Diameter: 2 to 3 mm. Upper surface color: Yellow-Green Group 144A. Lower surface color: Yellow-Green Group 144A.

*Rachis*.—Length: About 50 mm. Upper surface color: Yellow-Green Group 144A. Lower surface color: Yellow-Green Group 144A.

*Leaflet*.—Quantity: Normally 5 to 7 leaflets. Margins: Serrated. Size: Terminal leaflets are about 70 mm long, 41 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar122', substantially as illustrated and described herein, due to its abundant orange flowers, disease resistance, and extended period of bloom.

* * * * *